US011090601B2

(12) United States Patent
Lebon

(10) Patent No.: US 11,090,601 B2
(45) Date of Patent: Aug. 17, 2021

(54) CANISTER FOR CONTAINING AN ACTIVE AGENT

(71) Applicant: CLARIANT PRODUCTION (FRANCE) S.A.S., Choisy le Roi (FR)

(72) Inventor: Jacquy Lebon, Challands (FR)

(73) Assignee: CLARIANT PRODUCTION (FRANCE) S.A.S., Choisy le Roi (FR)

( * ) Notice: Subject to any disclaimer, the term of this patent is extended or adjusted under 35 U.S.C. 154(b) by 467 days.

(21) Appl. No.: 15/125,713

(22) PCT Filed: Mar. 4, 2015

(86) PCT No.: PCT/EP2015/054482
§ 371 (c)(1),
(2) Date: Sep. 13, 2016

(87) PCT Pub. No.: WO2015/139954
PCT Pub. Date: Sep. 24, 2015

(65) Prior Publication Data
US 2017/0001140 A1    Jan. 5, 2017

(30) Foreign Application Priority Data
Mar. 20, 2014    (EP) .................................... 14305392

(51) Int. Cl.
*B01D 53/04*    (2006.01)
*B01D 53/26*    (2006.01)
(Continued)

(52) U.S. Cl.
CPC ............ *B01D 53/0415* (2013.01); *A61L 9/00* (2013.01); *B01D 53/261* (2013.01);
(Continued)

(58) Field of Classification Search
CPC ... B29C 66/30221; B29C 65/02; B29C 65/00; B29C 65/08; B29C 65/58; B29C 65/72;
(Continued)

(56) References Cited

U.S. PATENT DOCUMENTS 3,107,838 A    10/1963    Brys et al.
3,223,278 A    12/1965    Allen
(Continued)

FOREIGN PATENT DOCUMENTS

CN    201775822 U    3/2011
CN    202508425 U    10/2012
(Continued)

OTHER PUBLICATIONS

English translation of Chinese Office Action dated May 3, 2017 with respect to parallel Chinese patent application No. 201580014668, along with Chinese Search Report dated Apr. 10, 2017—cited only for reference that is disclosed therein.
(Continued)

*Primary Examiner* — Anthony D Stashick
*Assistant Examiner* — James M Van Buskirk
(74) *Attorney, Agent, or Firm* — Scott R. Cox

(57) ABSTRACT

A canister containing an active agent wherein the canister includes a canister body having a peripheral body wall defining an upper opening and a non-removable snap-on cap. The cap includes a peripheral skirt. The peripheral body wall of the canister includes a step formed between a first portion of the peripheral body wall and a second portion located beneath the first portion. The first portion is thinner than the second portion to form the step, wherein an inner shape of the peripheral skirt and an outer shape of the first portion of the peripheral body wall form a snap-on fit, wherein the cap surrounds the first portion. A vertical extension of the peripheral skirt is smaller than a vertical
(Continued)

extension of the first portion of the peripheral body wall to form a gap between the step and the peripheral skirt.

17 Claims, 4 Drawing Sheets

(51) Int. Cl.
*A61L 9/00* (2006.01)
*B65D 81/26* (2006.01)

(52) U.S. Cl.
CPC ......... *B65D 81/264* (2013.01); *B65D 81/268* (2013.01); *B01D 53/0407* (2013.01); *B01D 2257/80* (2013.01)

(58) Field of Classification Search
CPC ... B29C 65/7855; B29C 66/71; B29C 66/727; B29C 66/9513; B29C 66/951; B29C 66/3022; B29C 66/30223; B29C 66/131; B29C 66/12461; B29C 66/114; B29C 66/112; B29C 66/53421; B29C 66/73921; B29C 66/5344; B29L 2031/712; B29K 2023/0633; B29K 2023/065; B01D 53/268; B01D 53/0415; B01D 53/261; B01D 2257/80; B01D 53/0407; B01D 2257/104; B65D 51/30; B65D 81/268; B65D 81/264; B65D 42/0212; B65D 81/266; B65D 2543/00092; B65D 2543/00296; B65D 2543/00407; B65D 2543/00518; B65D 2543/00537; B65D 2543/00555; B65D 2543/00574; B65D 2543/0062; B65D 2543/00685; B65D 2543/0074; B65D 2543/00796; A61L 9/00; F17C 11/00
USPC ............... 206/204; 220/784, 367.1, 373, 796
See application file for complete search history.

(56) References Cited

U.S. PATENT DOCUMENTS

| | | | |
|---|---|---|---|
| 3,999,677 A | | 12/1976 | Oberkircher |
| 4,093,105 A | | 6/1978 | Russell et al. |
| 4,385,706 A | | 5/1983 | Freeman |
| 5,096,836 A | * | 3/1992 | Macho ............. B01L 3/502707 422/423 |
| 5,149,343 A | * | 9/1992 | Sowinski ........... B01D 53/0415 95/127 |
| 5,191,721 A | | 3/1993 | Incorvia et al. |
| 5,221,000 A | | 6/1993 | Lee |
| 5,641,088 A | | 6/1997 | Berger |
| 5,730,785 A | | 3/1998 | Idol et al. |
| 5,759,241 A | | 6/1998 | Klett et al. |
| 8,622,850 B2 | * | 1/2014 | Narita ................ A63B 53/0487 473/329 |
| 8,800,809 B2 | | 8/2014 | Portier |
| 2005/0173044 A1 | | 8/2005 | Drummond et al. |
| 2019/0133355 A1 | * | 5/2019 | Davies ............. A47G 19/2266 |

FOREIGN PATENT DOCUMENTS

| | | |
|---|---|---|
| CN | 202724303 U | 2/2013 |
| WO | WO9633108 A1 | 10/1996 |

OTHER PUBLICATIONS

International Search Report with Written Opinion dated May 19, 2015 with respect to international application No. PCT/EP2015/054482.

International Preliminary Report on Patentability dated Sep. 20, 2016 with respect to international application No. PCT/EP2015/054482.

* cited by examiner

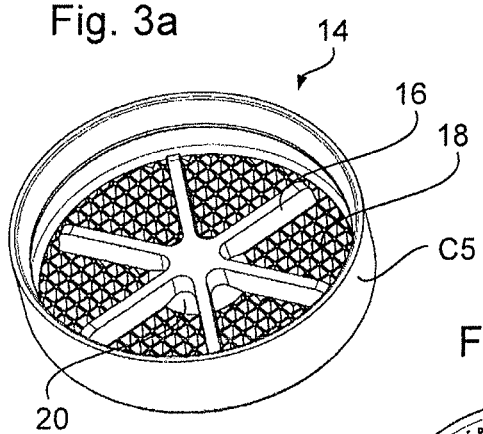
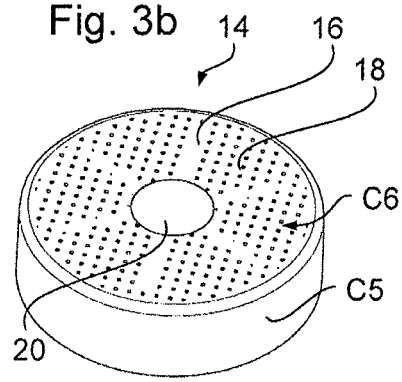
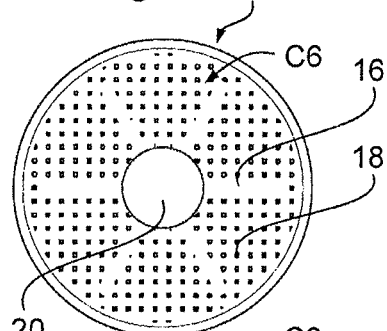
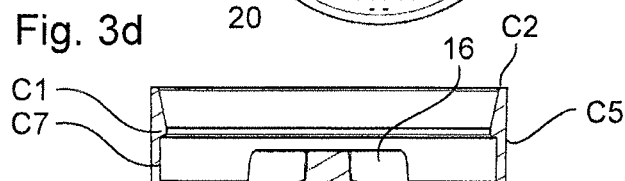
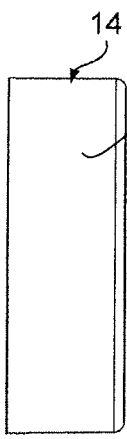
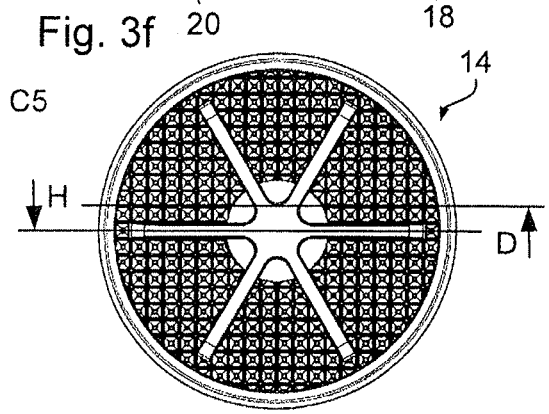
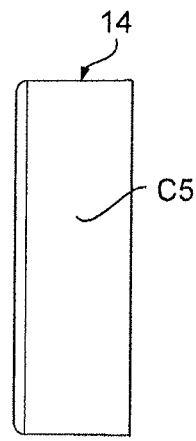
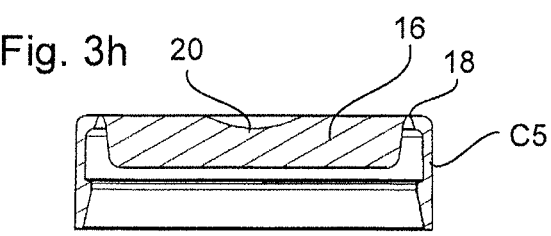

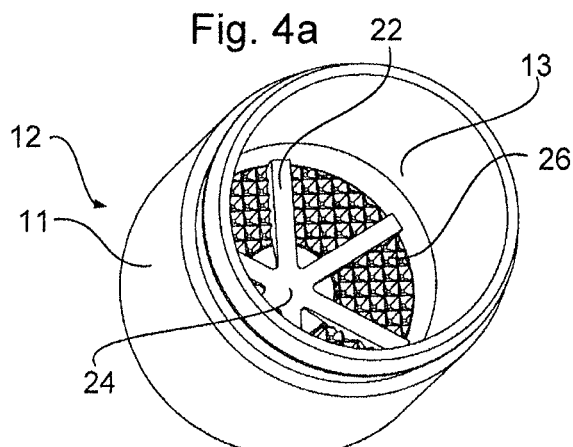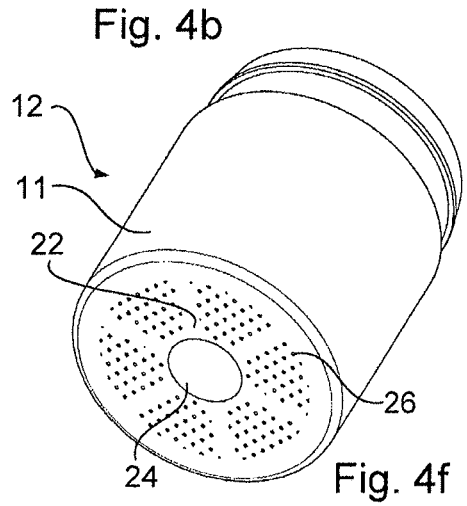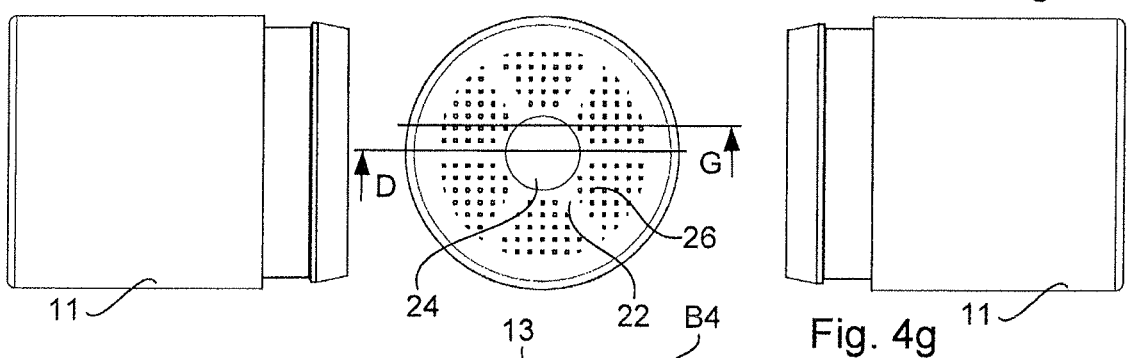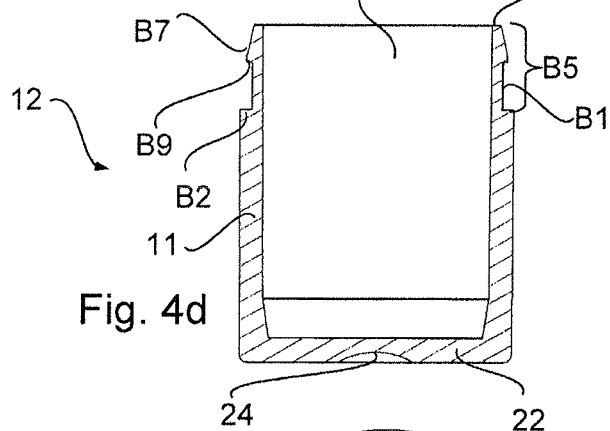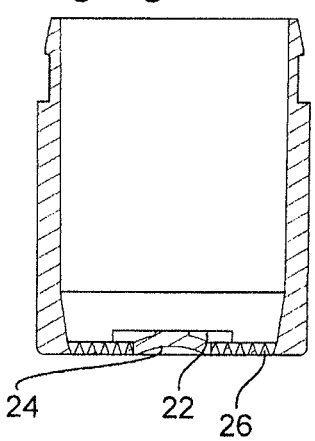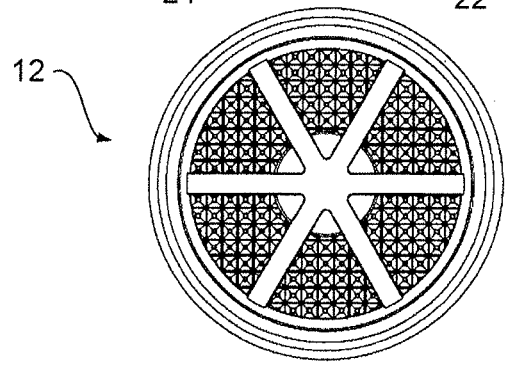

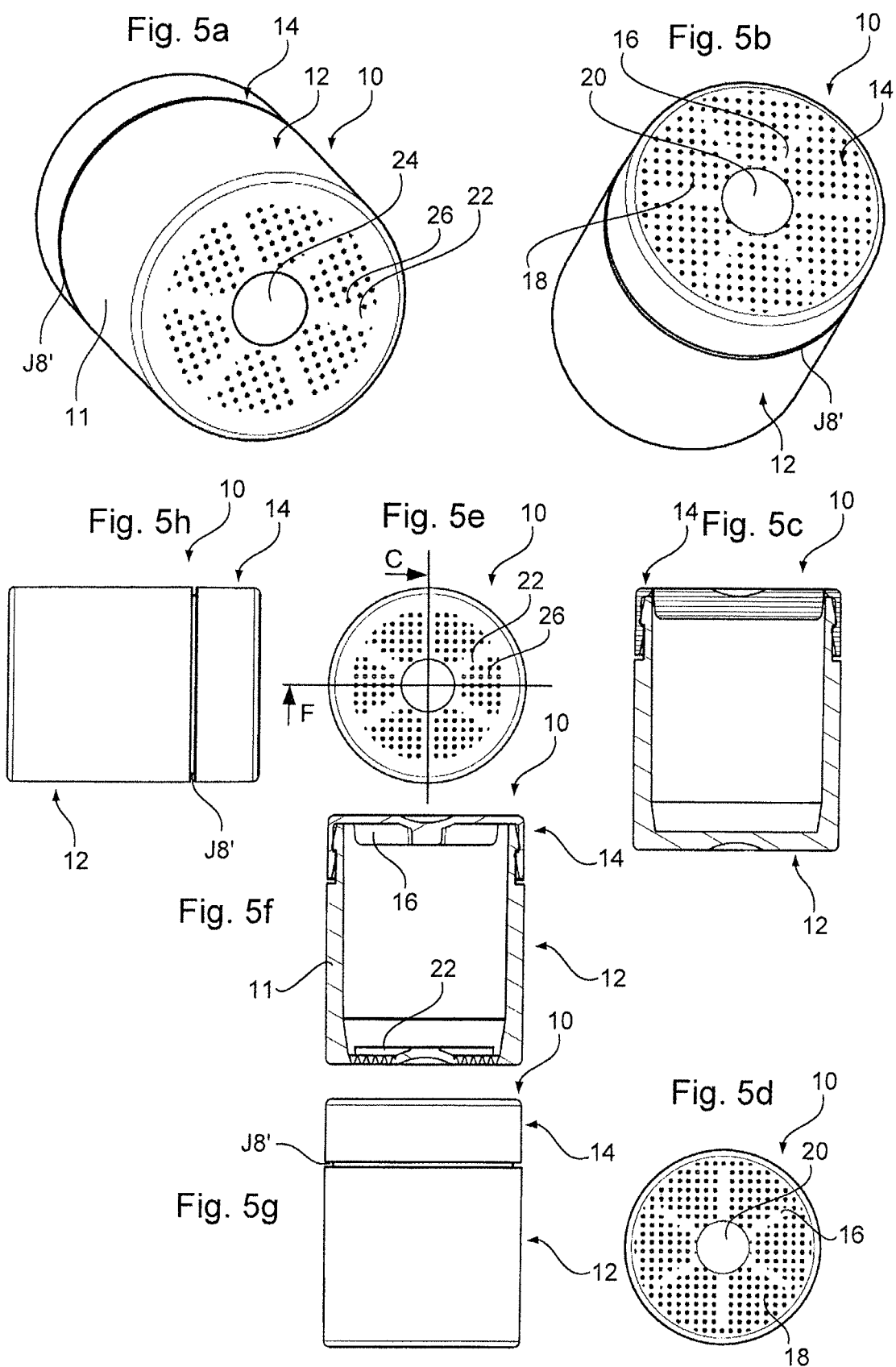

CANISTER FOR CONTAINING AN ACTIVE AGENT

TECHNICAL FIELD

The present invention relates to a canister for containing an active agent, such as a desiccant agent, an oxygen scavenger or a scented agent, and for allowing the active agent to interact with the environment of the canister, such as absorbing moisture, oxygen or odours, or releasing moisture or a fragrance, when the canister is closed. The present invention is, of course, applicable also to other active agents which are intended for purposely modifying the surrounding atmosphere inside a packaging in which the canisters of the invention are introduced.

The invention further relates to a method of manufacturing such a canister.

BACKGROUND OF THE INVENTION

Canisters according to the above-mentioned technical field are generally common and known to be placed inside of a package of goods for increasing the shelf life of the goods or substances which are sensitive to moisture, oxygen or other gases and contained in the package. Active agents such as a desiccant or oxygen scavenger are known in the art and allow absorbing moisture or oxygen from the inner space of such a package via perforations or permeable membranes of the canister being placed inside of the package.

Canisters of the art are usually cylindrically shaped and comprise two pieces, namely a body and a cap, being secured to each other when containing the active agent such as the desiccant or oxygen scavenger. A common means for securing the cap to the body is a snap-on connection, but also different means for securely connecting the cap and the body are known, for example other mechanical connections, crimping, fusion, welding and the like.

U.S. Pat. No. 5,759,241 discloses such a canister having a locking rib in an upper portion of the cylindrical outer wall of the body which is configured to snap into a recess in an upper cylindrical portion of a cap when the cap is secured onto the body.

A common problem of the canisters known from the art is that the cap may be accidentally opened or may pop off during storage or use of the canister inside of the package so that the active agent may be released or may leak out of the canister thereby contaminating the goods or substances contained in the package surrounding the canister. This popping off can, in particular in a snap-on connection, result from a deformation of the cap or the body under internal or external forces, for example if an external load is applied to the package which deforms the package and further acts on the canister.

Another source of undesired opening of the canister known from the art is that any variation in dimensional tolerance of the cap and the body—that should fit tightly—is detrimental for the quality and the reliability of the snap-on connection. Thus a label can be used to assist in preventing the snap-on connection from being accidentally disengaged, as for example disclosed in U.S. Pat. No. 5,759,241. However labelling represents an additional processing step and involves an additional component which may not be desired for cost reasons.

A further possible cause of the popping off of the canisters of the art can be in connection with filling the active agent into the canister, in particular if the active agent is in the form of a powder, small particles or particles which generate dust. When filling the canister body with the active agent via the upper opening, which usually is performed in a high-speed process, it can happen that a portion of the active agent sticks to the outer surface of the body in the vicinity of the opening, where a snap-on connection is formed between the cap and the body. If particles of the active agent are present at one of the surfaces cooperating to form the snap-on connection between the cap and the body, the quality and the reliability of the snap-on connection may be impacted or more easily destabilized.

SUMMARY OF THE INVENTION

The present invention aims at solving the above-mentioned problems with canisters of the art. In particular, the present invention aims at improving the quality and the reliability of the canister assembly and avoiding popping off of the cap from the canister body or an undesired opening of the closed canister, in particular when the canister is intended to be filled with an active agent in a high speed filling process.

The canister according to the present invention comprises a canister body having a peripheral body wall defining an upper opening for inserting the active agent into the canister and a non-removable snap-on cap cooperating with the canister body so as to close the upper opening of the canister body, wherein the cap comprises a peripheral skirt. According to the above description of the canister body, an opening being objectively suitable for inserting the active agent into the canister is located at the vertically uppermost position. Of course, it is also possible that this opening is located at the lowermost portion of the body or at a lateral location with respect to the remaining body depending on the orientation and the configuration of the canister. However, for facilitating the description of the canister, reference is made to an orientation and configuration of the canister where the opening is an upper opening. In the following description, a "vertical" or "axial" direction refers to the canister in its upright position. In this position, the vertical or axial direction is substantially parallel to a cylinder axis, if the canister comprises a generally cylindrical shape. Hence, the "lateral" or "radial" direction refers to a direction that is perpendicular to the "vertical" direction, e. g. from the cylinder axis towards the circumference of the canister.

The non-removable snap-on cap is a cap which is not intended to be removed by a user after the canister has been closed, particularly after having been filled with the active agent. Therefore, the cap does not need to comprise any opening means which would facility an opening step. It is even preferred that the cap is free of any means for removing the cap from the canister body. In other words, the present invention preferably relates to a cap which does not comprise any means for facilitating an opening step.

The peripheral body wall of the canister body comprises a step, stair or echelon formed between a first portion of the peripheral body wall located adjacent to the upper opening and a second portion of the peripheral body wall located beneath the first portion, wherein the first portion is at least partially thinner than the second portion so as to form the step. Preferably, the step extends along the complete circumference of the body wall, i. e. along the peripheral body wall so as to divide the first portion close to the opening from the second portion remote from the opening in an axial direction perpendicularly to the extension direction of the step. If the first portion is at least partially, preferably completely, thinner than the second portion so as to form the step, the skirt of the cap can be snapped onto the first portion without laterally or radially significantly extending beyond the peripheral surface of the second portion of the body wall, at least in the vicinity of the step. This is particularly helpful for avoiding any unintended opening of the cap. It is preferred that the peripheral skirt of the cap is of a thickness of about the difference in thickness between the first and the second portion of the peripheral body wall. However, it is not required for the peripheral skirt of the cap to be of this thickness. Rather, the skirt can also be thinner or thicker than the difference between the thicknesses of the first and second portion of the body wall.

The step preferably is an abrupt, kink-like transition from the first to the second portion of the peripheral body wall the surface of which extending substantially perpendicular to the vertical direction, i. e. the direction from the first to the second portion of the peripheral body wall, and substantially perpendicularly to the surfaces of the first and second portion next to the step. However, this step can also have different forms such as an inclined surface not perpendicularly to the vertical direction or can have a curved shape.

An inner shape of the peripheral skirt of the cap and an outer shape of the first portion of the peripheral body wall are adapted to form a snap-on fit between the cap and the canister body wherein the cap laterally surrounds the first portion.

Such a configuration is generally known in the art, for example from U.S. Pat. No. 5,759,241. For example, the first portion of the peripheral body wall may comprise a locking rib or projection and the peripheral skirt of the cap may comprise a corresponding recess. However, it is of course also possible that the skirt comprises a rib or projection and that the first portion of the body wall comprises the corresponding recess. In addition, also other geometrical shapes are possible and generally known in the art which allow for a snap-on connection between the cap and the body. In particular, it is possible that a plurality of snapping features is provided at both the first portion of the body wall and the peripheral skirt, for example a recess and a projection, two projections and two recesses, respectively or similar configurations. According to the present invention, the skirt of the cap laterally surrounds the first portion of the body. This means that, where the cap is snap fit to the canister body, the cap forms the outer surface of the canister while interacting with the canister body on its inner surfaces. Different configurations, such as the skirt of the cap being located on the inside of the peripheral body wall of the canister body, can be equivalent.

The vertical extension of the peripheral skirt is smaller than the vertical extension of the first portion of the peripheral body wall so as to form a gap between the step and the peripheral skirt when the cap is snapped onto the body. If the vertical extensions of the peripheral skirt and the first portion of the peripheral body wall are equal to each other or if the vertical extension of the peripheral skirt is larger than that of the first portion of the peripheral body wall, there will be no gap between a step between the first and the second portion of the peripheral body wall, on the one hand, and the skirt of the cap, on the other hand. In this configuration, when a vertical pressure is applied on the top portion of the cap during assembly of the cap and the body, the snap-on connection can be incomplete or unreliable because, when the peripheral skirt laterally deviates to pass across the snapping means of the canister, the lower edge of the peripheral skirt of the cap first contacts the step of the body leading to friction forces that can interfere with the proper placement of the snapping means, or e. g. if any foreign particles exist on the step. Furthermore, the configuration of the prior art requires further adjustments of the vertical pressure applied during assembly because excessive pressure could accentuate the radial deviation of the peripheral skirt and improve the risk of unfit placements of the snapping means.

On the contrary, in the canister of the present invention, the peripheral skirt of the cap can deviate during assembly until the top portion of the cap first contacts the uppermost part of the canister body without interference of the cap with the step of the canister or e. g. foreign particles on the step.

Accordingly, a more reliable assembly is allowed, which is furthermore independent of the vertical pressure applied during assembly of the cap and the body. Moreover, a reliable assembly is obtained which is less sensitive to the process of filling the canister with particles of active agent or to the filling conditions, contrary to the configuration of the prior art where any particles sticking to or remaining on the surface of the step or on the snapping means of the canister, in particular in full filling conditions, are detrimental to the quality and reliability of the snap-on connection between the cap and the canister body.

Preferably, the gap has a vertical dimension of greater than and including 0.05 mm, further preferable greater than and including 0.15 mm. This gap of at least 0.05 mm, preferably at least 0.15 mm allows for an increased reliability of a snap-on connection between the cap and the body. More particularly, the value of 0.05 mm is the minimal preferred dimension taking into account the variation in dimensional tolerance of the cap and of the body, for example when a little higher nominal value is sought.

Preferably, the gap has a vertical dimension of less than and including 1 mm, preferably less than and including 0.6 mm. According to this preferred embodiment, where the gap is at most 1 mm, preferably at most 0.6 mm in the vertical dimension of the canister, the distance between the lower edge of the peripheral skirt and the surface of the step, i. e. the size of the gap, is small enough for avoiding any removal of the cap from the canister body, unintended or not, for example by insertion of an object or a tool into the gap that could disengage the snap-on connection.

In a preferred embodiment and in addition to the gap provided between the step and the peripheral skirt when the cap is snapped onto the body, a residual space between all surfaces defining the snap-on connection means is provided. These spaces are provisioned to avoid any stress on the snap-on connection that would result e.g. from pressure applied during filling or assembling operations of the canister or from dimensional deviations at manufacturing, resulting in an improved reliability of the snap-on connection.

Preferably, the active agent is at least one of the group consisting of the following elements: a desiccant agent, a moisture releasing agent, an oxygen scavenger, active carbon, a scent releasing agent, or a mixture of two or more of these elements. Examples for desiccant agents are silica gel, molecular sieve, clay, zeolites of a mixture thereof. Oxygen scavengers are, for example, iron-based oxygen scavengers, organic oxygen scavengers, enzymatic scavengers, unsaturated polymers or a mixture thereof. These elements are particularly useful in packaging goods or substances which are sensitive to moisture or oxygen wherein their shelf lives are reduced, if these goods or substances are in contact with moisture or oxygen. However, the present invention is, of course, applicable also to other active agents which are intended for acting on the surrounding of the canister.

Preferably, at least one of the canister body and the cap has a cylindrical shape having a polygonal, circular or elliptical base. A cylindrical shape is defined by the shape of a base and an axial extension, wherein the present canister preferably has the shape of a circular cylinder. However, also other cylindrical and non-cylindrical, for example conical or partially spherical, shapes are generally possible for the canister, the canister body or the cap, respectively.

In a preferred embodiment, the cap comprises a disk-like top portion from which the peripheral skirt depends and the uppermost part of the peripheral body wall abuts to and is in contact with the top portion when the cap is snapped onto the canister body. The contact of the peripheral body wall and the top portion of the cap ensures that the content of the canister, i. e. the active agent, is securely kept inside of the canister without any risk of the active agent contaminating the outer surface of the first portion, the inner surface of the skirt or even leaking out of the canister. Further, the contact of the disk-like top portion and the body wall increases the stability of the canister when closed.

In a preferred embodiment, the canister body and/or the top portion of the cap is permeable to gas in order to allow fluid exchange between an inside of the canister and an outside of the canister. The materials composing the canister body and/or the cap can be selected with regard to the permeation properties of the material towards the gas to be adsorbed by the canister allowing molding a canister without any apertures or thickness reductions to purposely increase the fluid exchange.

In a preferred embodiment, at least one of the canister body and the cap comprises a plurality of apertures allowing fluid exchange between an inside of the canister and an outside of the canister for the active agent to interact with the environment of the canister. The fluid exchange preferably is the exchange of di-oxygen and/or humidity or any other gas inside of the package in which the canister is located. The apertures are sized so as to allow such fluid exchange, while preventing the active agent from leaking out of the canister. Alternatively or additionally, it is possible that the canister comprises a permeable membrane or is at least partially made of a material which is permeable to gases so that apertures are not essential for the canister to allow the active agent to interact with the environment of the canister. However, it is also possible that the canister comprises apertures in the cap, in the canister body, or both and, in addition, a permeable membrane. It is also possible that the canister comprises areas of smaller thickness to increase its permeability to gases.

Preferably, the cap comprises one or more support elements extending across the cap between opposing portions of the skirt, wherein the support elements define a clearance between their ends and the skirt which clearance is suitable to receive an uppermost portion of the body wall. Such support elements may be in the form of ribs forming discrete ends adjacent, and preferably perpendicular, to the inner surface of the skirt. More preferably, these ribs extend across the diameter of the cap. The distance between the inner surface of the skirt and the discrete ends of the respective support elements, i. e. the clearance, is dimensioned so as to receive an uppermost portion of the body wall, i. e. of the first portion. Receiving this uppermost portion of the body wall can form a tight fit or a simple fit. In any case, a lateral deformation of the canister body wall or the cap, respectively, can be reliably avoided by the support elements which increase the strength of the cap in the lateral or radial direction as well as the strength of the body wall if the uppermost portion of the body wall is received in the clearance between the support elements and the skirt of the cap.

In a preferred embodiment, there is a space between the ends of the support elements and the first portion of the body wall received in the clearance of the cap. Indeed, if the end of the support element is clamped against the first portion of the canister body, it could generate constraints that are unfavourable for the holding of the cap. More preferably, this space or distance between the ends of the support elements and uppermost portion of the body wall is more than zero and less than the distance between the apex of the projection of the peripheral skirt of the cap and the apex of the projection of the body wall. It allows a better holding of the cap after assembly. This particular configuration of the support elements creates buttresses that absorb any effort or constraint when an external pressure is exerted on the lateral side of the canister.

In a preferred embodiment, the ends of the support elements are downwardly inclined towards the direction opposed to the inner surface of the skirt. This inclination angle is preferably between 5 and 30° with respect to the direction of the body wall. In this manner, the assembly is easier as the inclination angle serves as a guide for receiving the uppermost portion of the body wall in the clearance during assembly.

In a preferred embodiment, at least one, preferably both of the inner shape of the peripheral skirt and the outer shape of the first portion of the peripheral body wall comprises an inclined transition surface between a recessed part and a projecting part, wherein the transition surface is preferably inclined at an angle of between 30° and 90° with respect to a vertical extension of the body wall and the skirt. The inclined transition surface of the cap and the inclined transition surface of the first portion of the peripheral body wall can be different but are preferably substantially equal. The projecting part which is also known as "rib" or "bead" counteracts with the recessed part so as to form the snap-on connection between the cap and the body. The shape of the recess and the projecting part or rib is generally not limited. However, in the preferred embodiment, there is a surface of a transition from the recessed part to the projecting part which is also known as a "flank" of the projecting part or recessed part and this surface is preferably not perpendicular to the vertical extension of the body wall and the skirt but inclined at a different angle, particularly preferred at an angle of between 30° and 90°. However, it is generally also possible that this transition or flank is curved. The inclined surface reduces the risk of material being unintentionally removed when the respective element, i. e. the cap or the body, is taken out of a mould in which it is formed, for example by injection moulding. Therefore, the integrity of the projection or recess can be more reliably ensured and, thus, the reliability of the snap-on connection of the cap and the canister body is increased.

In a preferred embodiment, the canister body and the cap are made of different plastic materials, for example such that the material of the cap is more elastic than the material of the canister body. In this preferred embodiment, it is more easily possible to snap the cap onto the canister body. In this case, the cap can be deformed more easily to snap onto the body during the assembly of the canister. However, it is also possible that both the canister body and the cap are made of the same material. In another embodiment, the canister body and the cap are made of different plastic materials that are selected with regard to the permeation properties of the materials towards the gases to be adsorbed by the canister.

Preferred materials are a thermoplastic material, for example polyolefin-based polymers. It is preferred that the canister is made by an injection moulding method.

The canister according to the above description allows for securely fitting a cap onto a canister body, in particular by a snap-on connection which allows filling the canister with an active agent and snapping the cap onto the canister body at high-speed. The specific configuration of the above-described canister allows for a reliable connection of these elements even when an external force acts onto the canister in its closed configuration. Indeed, the specific snap-on connection is neither affected by lateral pressure applied on the canister body, nor by vertical pressure applied on the top portion of the cap.

Furthermore, the specific snap-on connection allows for absorbing any variation in dimensional tolerances such that the quality and the reliability of the connection is no longer impacted.

Furthermore, the specific configuration of the snap-on connection is no longer affected by excessive pressure applied during assembly and does not require further adjustments on the intensity of this pressure Therefore, high-speed filling and assembling of the canister is more easily possible than for configurations known from the art. The holding force of the snap-on connection is not even affected by particles of active agents in the area where the snap-on connection is formed so that the cap more reliably holds onto the canister body. Therefore, the reliability of the snap-on connection is less sensitive to the process filling and assembling and does not require specific conditions or high precision filling to prevent any risk of dust on the surfaces involved in the snap-on connection. Finally, the canister of the present invention provides a more precise, more reliable and better controlled assembly, and is compatible with high-speed manufacturing processes.

A method of manufacturing a canister body according to the above description comprises an injection moulding process using at least two sliding elements or pins for forming the external side of the first portion of the canister body. Then, the canister body can be released from the mould after the slides are removed. These removing processes allow for manufacturing the canister both efficiently and in a high quality because the risk of damaging the relevant surfaces, in particular the outside surface of the first portion of the peripheral body wall, is considerably reduced, compared to a removing process by forcible ejection.

BRIEF DESCRIPTION OF THE DRAWINGS

FIGS. 3a to 3h illustrate different views of a preferred embodiment of a cap for a canister.

FIGS. 4a to 4h illustrate different views of an embodiment of a preferred body for a canister.

FIGS. 5a to 5h illustrate different views of a preferred canister comprising the cap according to FIG. 3 and the body according to FIG. 4.

DETAILED DESCRIPTION OF THE EMBODIMENTS

Figure 1:
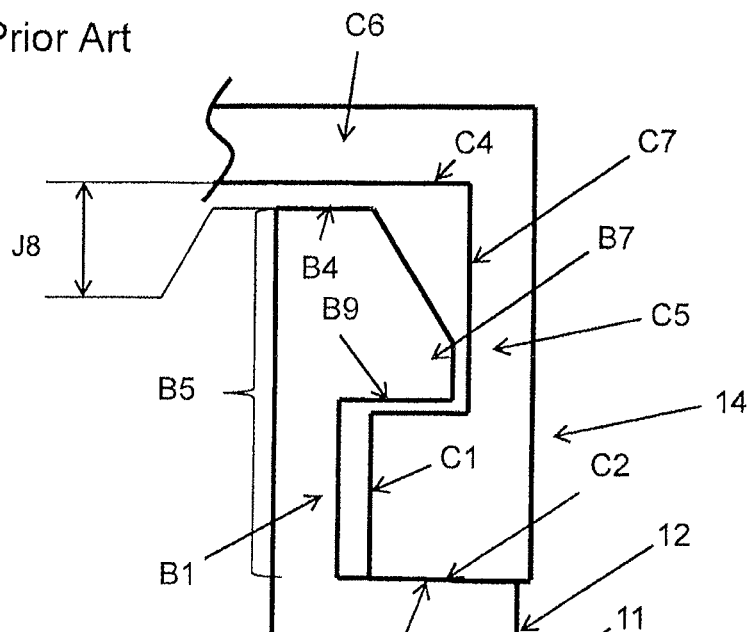
FIG. 1 shows a schematic drawing of a snap-on connection according to the prior art.

FIG. 1 illustrates an exemplary schematic drawing of the snap-on connection of canisters of the prior art. A body wall 11 of a canister body 12 comprises a first portion B5 located adjacent to an upper opening of the canister body and a second portion B6 beneath the first portion B5. The fist portion B5 comprise a projecting part B7 and a recessed part B1 as well as a step B2 between the first portion B5 and the second portion B6 which step B2 extends perpendicularly to the vertical extension of the canister body wall 11. An uppermost part B4 of the canister body wall Ills also illustrated in FIG. 1.

FIG. 1 further discloses a schematic illustration of a cap 14 which comprises a disk-like top portion C6 and a peripheral skirt 05. The skirt C5 comprises a projecting part C1 and a recessed part C7 and the projecting and recessed parts of the skirt C5 and the first portion B5, respectively, counteract in order to provide a snap-on connection between the cap 14 and the canister body 12.

In the configuration according to the prior art, the vertical extension of the skirt C5, i. e. the distance from the lower surface C4 of the top portion C6 of the cap to the lower edge C2 of the skirt C5, is larger than or equal to the vertical extension of the first portion B5, i. e. the distance from the step B2 to the uppermost part B4 of the body wall 11. This results in a gap J8 being formed between the uppermost part B4 of the canister body and the top portion C6 of the cap 14, more particularly a lower surface C4 of the top portion C6. On the other hand, a surface of the step B2 directly contacts a lower edge C2 of the skirt C5 of the cap 14. Such a structure sometimes shows problems of hindrance of the cap onto the body that may be due to a deformation of the skirt C5 when a vertical pressure is applied on the top wall C6 of the cap, leading to an easier disengagement of the snapping connection.

In the following description of preferred embodiments, reference is made to the figures wherein like elements are numbered by use of the same reference signs and a specific description of the same or corresponding elements in the different figures is omitted.

Figure 2:
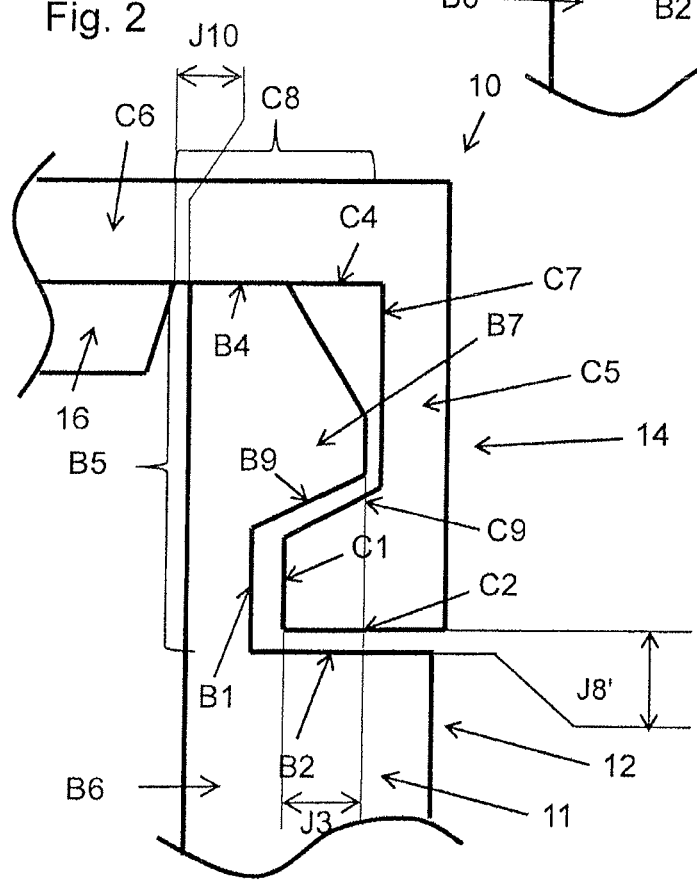
FIG. 2 illustrates a schematic drawing of a preferred embodiment.

FIG. 2 illustrates a preferred embodiment of a canister 10 for containing an active agent and for allowing the active agent to interact with the environment of the canister when the canister is closed. In contrast to the prior art configuration described above, the vertical extension of the peripheral skirt C5 is smaller than the vertical extension of the first portion B5 of the peripheral body wall 11 so as to form a gap J8' between the step B2 and the peripheral skirt C5 when the cap 14 is snapped onto the body 12. More precisely, the gap J8' extends between the surface of the step B2 and the lower edge C2 of the peripheral skirt C5. As can be seen in FIG. 2, the lower surface C4 of the top portion C6 contacts the uppermost part B4 of the peripheral body wall 11 of the canister body 12 and the skirt C5 depends from the top portion C6 of the cap 14.

The shape of the projection B7 of the body wall 11 and the projection C1 of the skirt C5 as well as the recesses C1, B1 of the skirt C5 and the body wall 11, respectively, are changed with regard to the prior art described before. A transition B9 in the first portion B5 is inclined with regard to the generally vertical extension of the body wall 11 at an angle of between 30 and 90°. Similarly, a transition C9 from the recess C7 to the projection C1 of the cap 14 is inclined at a similar angle with regard to the generally vertical extension direction of the peripheral skirt C5 of the cap 14. The angle of inclination of the transitions B9 or C9 is measured with respect to the vertical direction, more particular the upper part of a parallel to the cylinder axis of a generally cylindrical canister. FIG. 2 illustrates, in this sense, an inclination at an angle of about 45°.

In addition to the above features, the cap 14 comprises support elements 16 one of which is schematically illustrated in FIG. 2. These support elements 16 provide a clearance C8 between the peripheral skirt C5 and the end of the support elements 16. This clearance C8 is sufficiently sized to receive at least partially the first portion B5 of the body wall 11 so as to increase the canister's stability with regard to external, in particular lateral or radial, forces applied to the cap 14 or the canister body 12.

Furthermore, a space J10 between the ends of the support elements 16 and first portion B5 of the body wall received in the clearance C8 of the cap is more than zero and less than a distance J3 between the apex of the projection C1 of the peripheral skirt C5 of the cap and the apex of the projection B7 of the body wall.

FIGS. 3a to 3h show a preferred embodiment of a cap 14. FIGS. 3a and 3b are perspective views of the cap 14 illustrating the top portion C6, the skirt C5, a central portion 20 of the top portion C6, support elements 16 as well as apertures 18 which facilitate the passage of gases or other fluids between the inside and the outside of the canister when assembled for the active agent to act on the environment of the canister.

FIGS. 3c and 3f are a top and a bottom view of the cap 14, whereas FIGS. 3e and 3g are side views of the cap 14. FIG. 3d is a sectional view of the cap 14 taken along the line D in FIG. 3f. FIG. 3h is a sectional view taken along the line H in FIG. 3f.

FIGS. 4a to 4h illustrate different views of a preferred embodiment of a canister body 12. FIGS. 4a and 4b illustrate perspective views of the canister body 12. A bottom surface of the canister 12 comprises a plurality of reinforcing ribs 22 which provide a solid structure to the bottom of the canister body. Further, the bottom of the canister body 12 comprises a plurality of apertures 26 in order to facilitate the passage of gases or other fluids so that an active agent inside of the closed canister can interact with the environment of the canister. FIG. 4a further shows the canister body wall 11 and the upper opening 13. As can be taken from FIG. 4h, which is top view of the bottom surface of the canister body 12, the apertures 26 are similar to the apertures 18 provided in the cap 14. FIGS. 4e and 4f are side views of the canister body 12, FIG. 4c is a bottom view of the canister body 12 and FIGS. 4d and 4g are sectional views. FIG. 4d illustrates a sectional view taken along the line D indicated in FIG. 4c. FIG. 4g is a sectional view along the line G illustrated in FIG. 4c.

FIGS. 5a to 5h illustrate a preferred embodiment of a canister 10 composed of a canister body 12 and a cap 14. FIGS. 5a and 5b illustrate perspective views of the canister 10 showing the features already described before and illustrated in FIGS. 3 and 4. In addition to FIGS. 3 and 4, FIG. 5, e. g. FIG. 5a, illustrates the gap J8' between the skirt C5 of the cap 14 and the step B2 of the canister body 12. FIGS. 5g and 5h are side views of the assembled canister 10, FIG. 5d is a top view and FIG. 5e is a bottom view of the canister 10. FIG. 5c is a sectional view taken along the line C illustrated in FIG. 5e. FIG. 5f is a sectional view taken along the line F illustrated in FIG. 5e.

The preferred embodiment which comprises a gap J8' and optimized contact surfaces between the cap 14 and the body 12 allows for improved holding properties. The snap-fit connection is less affected by an imprecise filling or an assembling process of the cap and the body because the requirements of the assembling process concerning the cleanliness of the surfaces on the snap-on connection and of the pressure applied during assembly of the snap-on connection are much lower than for conventional canisters. Accordingly, it is no longer required to prevent dust or particles from sticking to the surfaces involved in the snap-on connection. Therefore, high-speed filling and assembling of the canister is easier and more efficient than for the configurations of the prior art. The holding force of the snap-on connection is less sensitive to particles of active agents in the area where the snap-on connection is formed so that the cap more reliably holds onto the canister body.

As comparative example, a canister of the prior art and two canisters of the present invention have been submitted to tests of opening. The test consists in placing a canister with its peripheral body wall lying on a dynamometer and submitting the peripheral body wall to the pressure of a blade that displaces downwardly (i. e. inwardly in the lateral direction of the body wall). The blade is moved by a distance of 5 mm, starting from the peripheral body wall, with a displacement speed of 100 mm per minute. The lateral force exerted by the blade by means of this motion is measured by the dynamometer during the displacement of the blade and, after the displacement is completed, it is observed whether the canister was opened or not.

24 canisters of the prior art according to the configuration shown in FIG. 1 further comprising support elements were submitted to the test described above. Of these 24 canisters, 12 were opened during the respective test.

Of the 24 canisters of the present invention having a transition B9 and C9 at an angle of 90° (manufactured by a process using slides), none of these canisters was opened at the end of this test, even though some of these canisters had been filled to the brim.

Of the 24 canisters of the present invention having a transition B9 or C9 at an angle of 75° (manufactured by a process without slides and where the canister are removed from the mould by forcible ejection), none of these canister were opened at the end of this test, even though some of these canisters had been filled to the brim.

The invention claimed is:
1. A canister for containing an active agent for allowing the active agent to interact with an environment of the canister, when the canister is closed, wherein
canister comprises:
a canister body comprising a peripheral body wall defining an upper opening for inserting the active agent into the canister body, and
a non-removable snap-on cap cooperating with the canister body so as to close the upper opening,
wherein the cap comprises a peripheral skirt,
wherein the peripheral body wall comprises a step formed between a first portion of the peripheral body wall, located adjacent to the upper opening, and a second portion of the peripheral body wall, located beneath the first portion, wherein the first portion is at least partially thinner than the second portion so as to form the step,
wherein an inner shape of the peripheral skirt and an outer shape of the first portion of the peripheral body wall form a snap-on fit between the cap and the canister body wherein the cap at least partially laterally surrounds the first portion,
wherein a vertical extension of the peripheral skirt is smaller than a vertical extension of the first portion of the peripheral body wall so as to form a gap between the step and a lower edge of the peripheral skirt when the cap is snapped onto the canister body,
wherein the gap has a vertical dimension greater than and including 0.05 mm, and
wherein an uppermost part of the peripheral body wall abuts to and is in contact with a lower surface of a top portion of the cap when the cap is in a configuration pressed against the canister body in an axial direction.

2. The canister of claim 1, wherein the gap has a vertical dimension of less than and including 1 mm.

3. The canister of claim 1, wherein the active agent is selected from the group consisting of a desiccant agent, an oxygen scavenger, active carbon, a scent releasing agent, and a mixture of two or more thereof.

4. The canister of claim 1, wherein at least one of the canister body and the cap has a cylindrical shape with the shape of a base selected from the group consisting of polygonal, circular and elliptical.

5. The canister of claim 1, wherein at least one of the canister body and the cap further comprises a plurality of apertures allowing fluid exchange between an inside of the canister and an outside of the canister when the cap is snapped onto the canister body so that the active agent can interact with the environment of the canister.

6. The canister of claim 1, wherein at least one of the canister body and the cap further comprises areas of smaller thickness allowing fluid exchange between an inside of the canister and an outside of the canister when the cap is snapped onto the canister body so that the active agent can interact with the environment of the canister.

7. The canister of claim 1, wherein the cap further comprises one or more support elements extending across the cap between opposite portions of the skirt, wherein the support elements define a clearance between the skirt and ends of the support elements which clearance is suitable to at least partially receive the first portion of the body wall.

8. The canister of claim 1, wherein at least one of the inner shape of the skirt and the outer shape of the first portion of the body wall comprises an inclined transition surface between a recessed part and a projecting part.

9. The canister of claim 1, wherein the canister body and the cap are made of different plastic materials such that the material of the cap is more elastic than the material of the canister body.

10. A method of manufacturing the canister of claim 1 comprising
injection molding the canister in a mold using at least two sliders, and
removing the canister from the mold, wherein the sliders are removed before the manufactured canister is removed from the mold.

11. A canister for containing an active agent for allowing the active agent to interact with an environment of the canister, when the canister is closed, wherein
the canister comprises:
a canister body comprising a peripheral body wall defining an upper opening for inserting the active agent into the canister body, and
a non-removable snap-on cap cooperating with the canister body so as to close the upper opening,
wherein the cap comprises a peripheral skirt,
wherein the peripheral body wall comprises a step formed between a first portion of the peripheral body wall, located adjacent to the upper opening, and a second portion of the peripheral body wall, located beneath the first portion, wherein the first portion is at least partially thinner than the second portion so as to form the step,
wherein an inner shape of the peripheral skirt and an outer shape of the first portion of the peripheral body wall form a snap-on fit between the cap and the canister body wherein the cap at least partially laterally surrounds the first portion,
wherein a vertical extension of the peripheral skirt is smaller than a vertical extension of the first portion of the peripheral body wall so as to form a gap between the step and a lower edge of the peripheral skirt when the cap is snapped onto the canister body,
wherein the gap has a vertical dimension of less than and including 1 mm, and
wherein an uppermost part of the peripheral body wall abuts to and is in contact with a lower surface of a top portion of the cap when the cap is in a configuration pressed against the canister body in an axial direction.

12. The canister of claim 11, wherein the active agent is selected from the group consisting of a desiccant agent, an oxygen scavenger, active carbon, a scent releasing agent, and a mixture of two or more thereof.

13. The canister of claim 11, wherein at least one of the canister body and the cap has a cylindrical shape with the shape of a base selected from the group consisting of polygonal, circular and elliptical.

14. The canister of claim 11, wherein at least one of the canister body and the cap further comprises a plurality of apertures allowing fluid exchange between an inside of the canister and an outside of the canister when the cap is snapped onto the canister body so that the active agent can interact with the environment of the canister.

15. The canister of claim 11, wherein at least one of the canister body and the cap further comprises areas of smaller thickness allowing fluid exchange between an inside of the canister and an outside of the canister when the cap is snapped onto the canister body so that the active agent can interact with the environment of the canister.

16. The canister of claim 11, wherein the cap further comprises one or more support elements extending across the cap between opposite portions of the skirt, wherein the support elements define a clearance between the skirt and ends of the support elements which clearance is suitable to at least partially receive the first portion of the body wall.

17. The canister of claim 11, wherein at least one of the inner shape of the skirt and the outer shape of the first portion of the body wall comprises an inclined transition surface between a recessed part and a projecting part.

* * * * *